United States Patent [19]
Dey et al.

[11] Patent Number: 5,897,525
[45] Date of Patent: Apr. 27, 1999

[54] PROCESS AND APPARATUS FOR INTRODUCING A FLUID

[75] Inventors: Uwe Dey; Bernd Müller; Peter Hartwig, all of Berlin; Torsten Thiel, Fürstenwalde, all of Germany

[73] Assignee: Dey, Uwe and Mueller, Bernd, Berlin, Germany

[21] Appl. No.: 08/616,554

[22] Filed: Mar. 15, 1996

[30] Foreign Application Priority Data

Mar. 15, 1995 [DE] Germany .............................. 195 10 712

[51] Int. Cl.⁶ .................................................. A61M 31/00
[52] U.S. Cl. .................................. 604/67; 604/65; 604/66
[58] Field of Search ................................ 604/65, 66, 67, 604/30, 31, 23, 26, 49

[56] References Cited

U.S. PATENT DOCUMENTS

| | | | |
|---|---|---|---|
| 5,152,745 | 10/1992 | Steiner et al. | 604/23 X |
| 5,328,458 | 7/1994 | Sekino et al. | 604/65 X |
| 5,360,396 | 11/1994 | Chan | 604/23 X |
| 5,423,741 | 6/1995 | Frank | 604/23 X |
| 5,439,441 | 8/1995 | Grimsley et al. | 604/26 |
| 5,549,546 | 8/1996 | Schneider et al. | 604/23 X |

FOREIGN PATENT DOCUMENTS

| | | |
|---|---|---|
| 0 316 593 | 5/1989 | European Pat. Off. . |
| 0 517 190 | 12/1992 | European Pat. Off. . |
| 7508556 | 12/1975 | Germany . |
| 3413631 | 10/1985 | Germany . |
| 3611018 | 6/1987 | Germany . |
| 37 18 717 | 12/1988 | Germany . |
| 40 19 239 | 12/1991 | Germany . |
| 42 40 758 | 6/1993 | Germany . |
| 42 33 849 | 4/1994 | Germany . |

*Primary Examiner*—Wynn Wood Coggins
*Assistant Examiner*—N. Kent Gring
*Attorney, Agent, or Firm*—Venable; George H. Spencer; Catherine M. Voorhees

[57] ABSTRACT

Process for introducing a fluid into a cavity or a blood vessel of a human or animal body, particularly for gas insufflation in preparation for or during a minimally invasive surgical procedure or investigation of the body cavity or blood vessel, the fluid being conveyed from a pressurised gas store (11,12) through a fluid supply line (4) and an introduction instrument (T) of a fluid introduction system (1) into the body cavity or blood vessel and the internal pressure produced in the body cavity or blood vessel being determined from the insufflation pressure measured at a measuring point in the fluid introduction system and a correction magnitude reflecting the drop in pressure between the measuring point and the body cavity or blood vessel, wherein the internal pressure is determined substantially without interrupting the introduction of fluid from substantially continuously detected measurements of the insufflation pressure and the fluid volume introduced per unit of time (fluid flow), the gas flow yielding the correction magnitude on the basis of a predetermined non-linear characteristic which reflects the functional correlation between the fluid flow and the fall in pressure in the fluid introduction system.

14 Claims, 1 Drawing Sheet

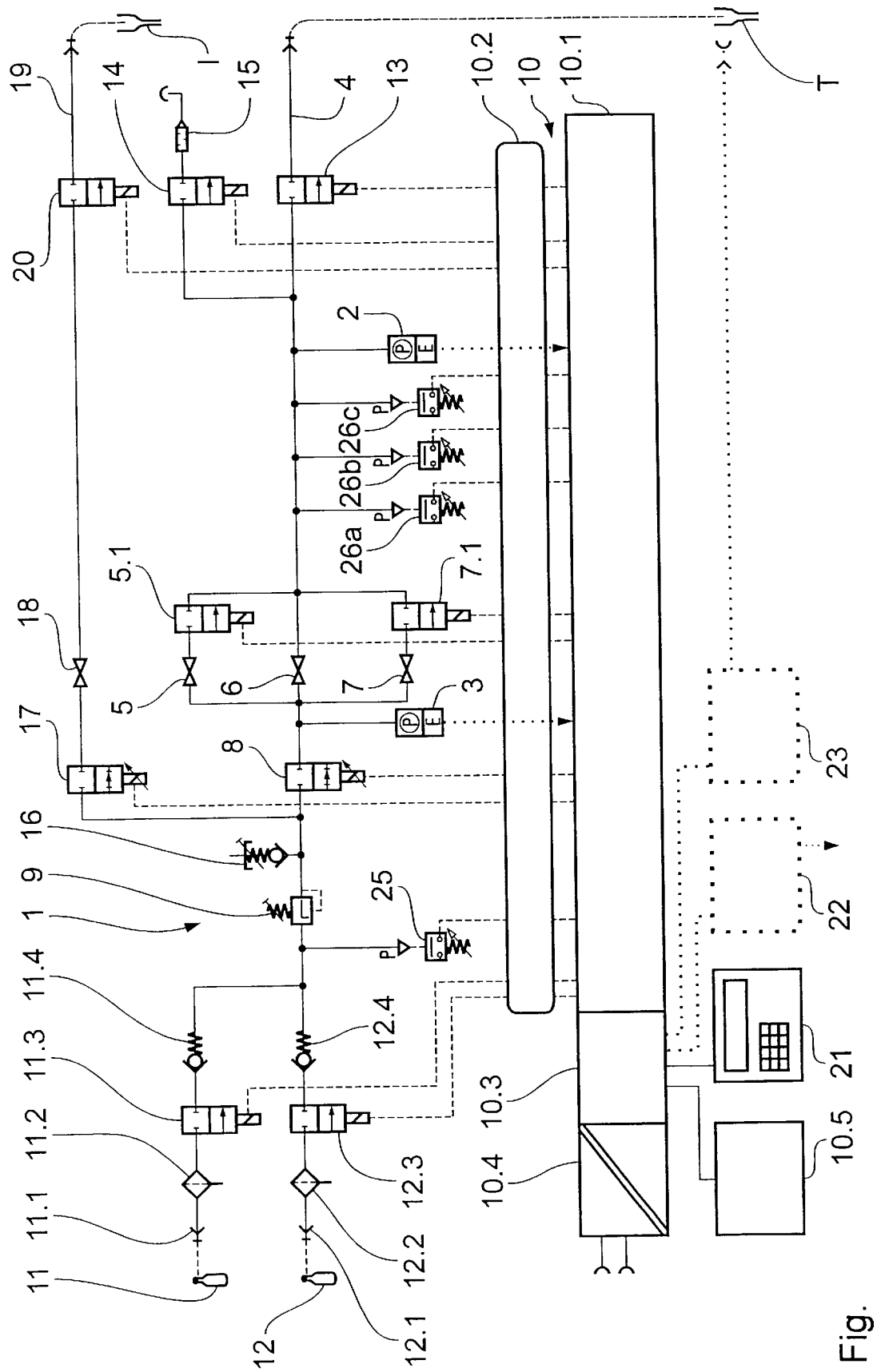

PROCESS AND APPARATUS FOR INTRODUCING A FLUID

BACKGROUND OF THE INVENTION

The invention relates to a process for introducing a fluid into a cavity or a blood vessel of a human or animal body, particularly for gas insufflation in preparation for or during a minimally invasive surgical procedure or investigation of the body cavity or blood vessel and an apparatus for performing the process.

In endoscopic interventions in human or animal bodies, for example in the abdominal region (in laparoscopy), the uterus (in hysteroscopy) or the joints (in arthroscopy) it is necessary to expand the cavity by means of a gas, for which carbon dioxide is preferably used. The space thus produced gives a sufficiently large operating and observation area enabling the operator to carry out the necessary medical interventions through suitable means of access to the body cavity.

During an operation or investigation a substantially constant internal pressure must be maintained in the body cavity since pressure fluctuations cause movements in the walls of the body cavity which can considerably disrupt the surgeons work or even make it impossible.

In order to maintain a constant pressure when introducing a gas into a part of the body which is to be treated medically, various pressure regulating circuits have been proposed which differ substantially in the nature and method of measurement and the place where the pressure measurement is carried out.

German patent 36 11 018 proposes an apparatus for insufflating gas, which has an insufflation instrument attached to a gas supply line. In the gas supply line are a pressure reducer, a flow meter and a pressure sensor arranged in series.

A control circuit switches the pressure reducer, as a function of a timer, in order to vary the working pressure in the gas supply line. The apparatus thus works intermittently in insufflation phases and measuring phases, whilst in the latter the supply of gas into the body cavity is reduced or interrupted and the intra-abdominal (static) pressure can then be measured substantially by means of the pressure sensor. Depending on the measurement obtained the electronic control circuit will automatically decide whether insufflation is to be continued with an increased insufflation pressure or—once the desired level of internal pressure is reached—the apparatus is subsequently operated at a reduced insufflation pressure in a so-called maintaining mode.

The solution described above has the serious disadvantage that the actual insufflation process is frequently interrupted in order to carry out the measurements until the desired internal pressure is reached. The need for regular monitoring of a constant pressure also requires further measuring phases even after the nominal pressure has been reached.

However, each interruption in the insufflation of gas will lead to a detrimental pulsing in the hollow organ in question which will interfere with the surgical procedure to a greater or lesser extent. In addition, the constant interruption to the supply of gas, particularly during the initial phase of insufflation, leads to a considerable reduction in the quantity of gas insufflated, with the result that the gas throughput per unit of time (gas flow) required for certain applications cannot be achieved and even in less demanding applications a long insufflation period is needed before the nominal pressure is achieved. A delay of this kind may be a considerable operating risk in certain cases.

Furthermore, it is known from German Utility Model 75 08 556 to carry out the introduction of gas into a body cavity and measurement of the corresponding intra-abdominal pressure through various means of access to the body cavity in order to be able to carry out pressure measurement and the introduction of gas simultaneously. This solution has the disadvantage that another incision has to be made into the body cavity for the measuring sensor. This is an additional burden on the patient and may in some cases lead to an uncontrolled escape of gas. Furthermore, because the access for the measuring sensor occasionally lead into the fatty tissue or an adjacent part of the body cavity to that where the insufflation is being carried out, there is the risk of mismeasurement with all its consequences.

DE-OS 34 13 631 describes an apparatus for non-intermittent insufflation of a gas. It has, inter alia, a measuring device for measuring the speed of the gas flow and a measuring device for measuring the pressure in the gas supply line used for the insufflation. The flow resistance of the insufflation line is determined by means of the speed of the gas flow and the actual intra-abdominal pressure is calculated therefrom, taking into account the constantly measured tube pressure, in an electronic evaluation circuit. However, this solution has two serious disadvantages:

On the one hand, the resistance level of the insufflation line is determined only once, ie. at the start of insufflation. This means that any change in the characteristics of the insufflation system, e.g. a change of insufflation instrument, is not taken into account. On the other hand, when measuring the intra-abdominal pressure, there is a presupposition that there is a linear correlation between the drop in pressure through the insufflation line and the corresponding flow quantity (gas flow). However, this linearity occurs fundamentally only in a limited range of gas flow values and is only approximate. With a higher gas throughput, in particular, this precondition does not apply, as has been confirmed by experimental tests, and in the process described above, erroneous results would be obtained for the internal pressure of the body cavity or organ.

The erroneous values obtained under the false assumption of a linear correlation between the fall in pressure and gas flow for the intra-abdominal pressure in insufflation results in a substantial risk of injury to the patient, particularly when a fairly large quantity of gas is being insufflated per unit of time. This danger consists in particular in over-extension of the insufflated organ, cavity or blood vessel, which might in some cases be irreversible.

The use of the methods described above are generally subject to strict limits, with the present degree of progress of minimally invasive medicine, as a result of the fact that shorter and shorter treatment times and higher insufflation rates are required whilst maintaining a very constant pressure level, the latter presupposing an exact and virtually continuous measurement of the internal body pressure.

SUMMARY OF THE INVENTION

The aim of the invention is therefore to provide an improved process of the kind mentioned hereinbefore and a technically simple apparatus for performing the process, by means of which a fluid can be introduced into a cavity or blood vessel and the internal pressure in the cavity or blood vessel expanded by the fluid can be measured with a high degree of accuracy and at a higher effective fluid throughput per unit of time while avoid undesirable pressure fluctuations.

This objective is achieved by a process wherein the internal pressure is essentially determined, without interruption to the introduction of fluid, from the insufflation pressure which is measured substantially continuously, as is the volume of fluid introduced per unit of time (fluid flow), and a correction magnitude reflecting a drop in pressure between a measuring point and the body cavity or blood vessel is determined by taking into account a stored non-linear correlation, predetermined in the working area, between the fluid flow and the drop in pressure between the measuring point and the body cavity or blood vessel.

Likewise, the objective is achieved in an apparatus having a fluid supply line connected to a pressurized fluid store, this fluid supply line being associated with a pressure regulating device and, downstream thereof, a first pressure sensor which serves to determine the insufflation pressure, and with a processing and control unit connected at the input end to the output of the pressure sensor and at the output end to a control input of the pressure regulating device, and further including a fluid flow measuring device which is associated with the fluid supply line and wherein the processing and control unit has a characteristic or table memory for storing at least one fluid flow correction characteristic or table and an internal pressure calculating unit connected at the input end to the output of the fluid flow measuring device and connected to the output of the characteristic or table memory. The term "fluid" means a gas or liquid in the instant specification.

The invention includes the finding that advantageous improvements in maintaining a constant pressure and the possibility of increasing the rate of insufflation are obtained, in the insufflation of fluids if the non-linearity, (preferably an approximately quadratic dependency) of the fall in pressure caused by the flow resistance of the insufflation system as a function of the flow volume used for insufflation fluid flow) is taken into account when determining the static pressure in a hollow organ expanded by insufflation or in a blood vessel acted upon by gas or liquid.

In accordance with the process of the invention, the internal pressure required for surgically expanding a cavity or permissible in an investigation (particularly in digital subtraction angiography) is determined without any separate measurement by suitable correction of the insufflation pressure measured substantially continuously (at the fluid supply line in the apparatus) with a correction magnitude which reflects the fall in pressure caused by the special insufflation system (including the trocar or veress needle) and the flow-dependent dynamic pressure component.

The correction magnitude dependent on the gas throughput per unit of time of the gas introduced, (gas flow) is taken as a characteristic of a predetermined non-linear characteristic which reflects the functional correlation between the gas flow and the flow resistance of the special insufflation system, or from a corresponding table. (Where this specification speaks of a "characteristic" this also includes the use of discontinuous storage means which store a corresponding non-linear correlation in the form of a table, so that processing can be carried out with conventional programmable computing means.)

Technical measurements have shown that the characteristic curve is essentially parabolic and conforms to the equation $$\Delta p = K \times Q^z$$

$\Delta p$ designating the pressure drop in the insufflation system, Q denoting the gas flow measured and K or z being constants which reflect the flow properties arising from the geometry of the gas supply line or the attached insufflation instrument, e.g. a trocar or a veress needle.

For various trocars and/or connecting tubes, for example, there is a family of characteristics which can be determined in advance and stored in the equipment, at least for the components which are used frequently. The choice of characteristic curve belonging to the particular insufflation system used can be made by manual inputting in the equipment or—preferably before the start or during the first phase of the introduction of the fluid—by a calibrating measurement.

In the latter case a single variation is carried out to the gas flow values, the two values for the insufflation pressure and the associated gas flow values being stored, the difference between the values being formed and the relevant stored characteristic being determined with the pair of values obtained, i.e. selected as the characteristic correct for the system. In the gas flow, the higher value can also be used instead of the difference if this higher value is sufficiently greater than the lower value.

If the value of z is known in advance (equal to 2, for example) the quotient of the two differences (or of the pressure difference and the higher gas flow value) can also be obtained, thereby obtaining the above-mentioned constant K.

The calculation is made in a microcomputer having a characteristic memory from which the data representing the family of characteristics are retrieved for a computer-aided comparison of the measurements obtained during gas flow variation.

The two constants K and z can be determined on the one hand, when changing the insufflation instrument, by insufflating twice against the ambient pressure from two pairs of measurements or, on the other hand, for a variety of gas supply lines and insufflation instruments by means of a series of calibrating measurements.

In this way it is possible to determine the drop in pressure as a function of the fluid flow beforehand experimentally, for all kinds of practically usable modifications of the insufflation system, and to store these values in readiness.

The correction magnitude which represents the flow resistance of the insufflation system comprising an insufflation line and an insufflation instrument connected thereto, always has to be determined again, if the insufflation instrument is changed, resulting in changes in the cross-section and/or changes in the length of tubing and resistances.

The apparatus for performing the process according to the invention comprises in particular a device for (preferably continuously) measuring the fluid throughput per unit of time and a memory device for recording the characteristic value or values, by means of which the correction magnitude for indirectly determining the internal body pressure can be calculated from the fluid flow measured.

In one particularly economical embodiment the first pressure sensor for determining the insufflation pressure in order to produce the flow measuring device has a second pressure sensor associated with it, and between the measuring points of the two pressure sensors in the supply line is a flow resistance element. This generates a defined fall in pressure or differential pressure from which the volume throughput per unit of time (flow value) is then determined in a manner known per se.

A substantial advantage of the apparatus for performing the process is the double function of the first pressure sensor which is used both to determine the differential pressure in order to calculate the fluid flow and also at the same time gives the actual value of the insufflation pressure.

There is therefore no need to provide a separate, relatively expensive differential pressure sensor.

The pressure values obtained by means of the first and second pressure sensors are used to form a differential pressure and, in order to calculate the fluid flow value, they are supplied to the processing unit which is provided with hardware or software in order to perform the calculation. The flow values form the basis for calculating the internal pressure in the organ, body cavity or blood vessel acted upon by the gas, especially carbon dioxide, as explained above, together with the insufflation pressure in the apparatus which is measured at the same time.

According to a favourable embodiment of the invention which allows versatile use of the apparatus in a wide range of very small gas throughputs (up to 0.1 l/min in hysteroscopy) through moderate (around 2 l/min in arthroscopy) up to very great gas throughputs (up to about 30 l/min in laparoscopy), a plurality of parallel connected flow resistance elements are provided in order to expand the range of measurements.

These flow resistance elements, which may take the form of shutters or sintered material inserts, for example, are each arranged in a branch line of the gas supply line which can be closed off by means of controllable valves. By electrically actuating the valves using the microcontroller and the control unit of the apparatus it is readily possible to switch over the measuring range, which can be determined by the nature and number of shutters or sintered inserts in one or more branches of the tube.

In addition, the processing unit preferably has means for calculating and storing one or more of the characteristic curves required for the calculation.

Moreover, the arrangement of the pressure sensors is advantageously suitable, in conjunction with the processor unit, for checking the correct operation of the pressure sensors while the apparatus is working, by means of a plausibility control. For this purpose, the processor unit contains special electronic means which constantly or at least periodically check the sensors by comparing them with one another.

According to an advantageous embodiment of the invention this is carried out by pressure comparison in the operating states of the apparatus in which no gas is flowing from the apparatus, i.e. the drop in pressure at the gas flow measuring device shows the value "0". In this case, correctly operating pressure sensors will show the same measurement. Similarly, it is also possible to increase or reduce the gas flow slightly from time to time during the introduction of gas. The resulting pressure wave must be indicated at a substantially constant level in correctly operating pressure sensors.

A plausibility control of this kind advantageously does away with the need for a third pressure sensor as a safety pressure monitor at the outlet of the apparatus.

According to another advantageous feature of the invention the pressurised gas store of the apparatus has at least two gas bottles which can be alternately connected to the gas supply line via switching means. The switching means take the form of a solenoid with a non-return valve provided upstream of them and are controlled by means of the processor unit as a function of the pressure conditions in the gas supply line.

One advantageous possibility for keeping clean the surgical or diagnostic instruments in minimally invasive surgery offers an embodiment of the apparatus in which the fluid supply line has, in addition to the outlet opening into the insufflation trocar, an additional outlet through which fluid can be introduced into a medical instrument. This largely prevents the entry of body fluid into the instrument. Appropriately, a controllable valve for selectively closing off the outlet and optionally for adjusting the gas throughput per unit of time may be provided in front of the additional outlet.

The apparatus may also have an associated device for treating, particularly heating, humidifying and/or filtering, the fluid, particularly close to the insufflation instrument, and this treatment device may also be controlled by means of the processing and control unit of the basic apparatus.

According to another further feature of the apparatus described, the processing unit may have an associated interface through which the current insufflation data, such as the level of internal pressure determined according to the invention, the gas flow value or the total amount of insufflated gas, can be displayed on a video screen which is available to the operator for monitoring the field of operation. In the interests of clarity it is advisable to display the values intermittently or only when there is a change which exceeds a certain amount. Similarly, by means of an additional interface it is possible to display data from other equipment also used in the operation on the video screen.

Advantageous further features of the invention are described more fully hereinafter together with the description of the preferred embodiment of the invention with reference to the drawing.

BRIEF DESCRIPTION OF THE DRAWING

The drawing shows a basic circuit diagram of a preferred embodiment of an arrangement for carrying out the process according to the invention.

DETAILED DESCRIPTION OF THE INVENTION

The insufflation device shown diagrammatically in the drawing for insufflating carbon dioxide before and during diagnostic or surgical procedures, in which the internal pressure prevailing in the body cavity or blood vessel is continuously determined and regulated, has a pressurised gas store with two gas bottles 11 and 12 the connections 11.1 and 12.1 of which are each attached to a gas supply line 4 via a filter 11.2 and 12.2, a solenoid 11.3 and 12.3 and a non-return valve 11.4 and 12.4.

Attached to the free end of the gas supply line 4 is an insufflation instrument T for introducing the gas into the body of the person or animal.

In the gas supply line 4, downstream of the gas bottles, for monitoring the pressure therein, there is a high pressure switch 25 the output of which is connected to a processing unit 10 of the equipment. In the event of a deficiency of gas in the particular gas bottle 11 or 12 connected to the gas supply line 4, there is an appropriate optical and/or acoustic signal by means of the processing unit 10 and an associated operating and display area 21. The other bottle 12 or 11 can then be connected up to the gas supply line either manually or automatically, if the warning signal having been processed by the processor unit and converted in the associated control unit 10.2 is simultaneously used as a control signal for the solenoid 11.3 or 12.3.

A high pressure reducer 9 provided downstream, having an excess pressure safety device 16, reduces the gas pressure in the gas supply line 4 to a level in the lower bar region. If the high pressure reducer 9 fails an overpressure safety device 16 downstream thereof is actuated and opens the gas supply line 4 to atmosphere.

A proportional valve 8 provided downstream of the high pressure reducer 9 and the overpressure safety device 16 is operated in cooperation (as described more precisely hereinafter) with pressure sensors 2 and 3 (arranged further downstream) as a pressure regulating device, the proportional valve 8 being actuated via the microcomputer (microcontroller) 10.3 and the control part 10.2 of the processor unit 10.

The pressure sensors 2 and 3, the outputs of which are connected to separate inputs of the processor unit 10 (more accurately: the analogue processing part 10.1) form a differential pressure gauge together with flow resistors 5, 6, 7 arranged between them and connected in parallel to one another in branches of the gas supply line.

The gas flow present in the gas supply line 4 is calculated in the processing unit from the pressure values obtained upstream and downstream of one of the flow resistors. The flow resistors 5, 6, 7 connected in parallel are each constructed as a calibrated shutter or sintered insert with greatly differing flow resistance levels and can be switched on or off by actuation of a solenoid 5.1 or 7.1 provided in the corresponding branch of the tube, by means of the operating area 21 and the microcontroller 10.3. In this way the measuring range can easily be switched over so that a gas flow ranging from a few tens of millilitres up to about 40 liters per minute can be measured.

The pressure sensor 2 mounted downstream of the flow resistors serves simultaneously to detect the insufflation pressure.

A major advantage of the apparatus 1 for gas insufflation shown is the double function of this pressure sensor which is used—together with the second pressure sensor 3 instead of a conventional differential pressure sensor—to determine the differential pressure in order to calculate the gas throughput per unit of time (gas flow) and also at the same time sends the actual value of the insufflation pressure to the processor unit 10.

In the processor unit 10 the pressure sensor signals are prepared and the gas flow value is calculated from the difference between the pressures determined by the first and second pressure sensors. In addition, as described above, the appropriate characteristic curve for the specific insufflation system is selected here in order to determine the internal pressure from a plurality of characteristic curves stored in a characteristic memory 10.5 for the functional correlation between the drop in pressure caused by the insufflation system (more precisely that part which extends from the measuring point of the pressure sensor 2 to the patient's body) and the gas flow.

Finally, the internal body pressure to be determined here is calculated from the insufflation pressure measured and the fall in pressure taken from the appropriate characteristic curve for the gas flow which is measured (indirectly by means of the pressure sensors 2 and 3) and this is displayed on the operating and display field 21 and fed into the control part 10.2 in order to operate the proportional valve 8. This operation is such that when the internal pressure values are significantly below the nominal internal pressure (during the initial phase of insufflation) a major gas throughput is achieved, whereas once the nominal internal pressure is reached there is merely sufficient insufflation to maintain the pressure with a substantially reduced gas throughput.

Moreover, the arrangement of the pressure sensors 2, 3 and the (hard- and software) construction of the microcontroller 10.3 is such that the operation of the pressure sensors 2 and 3 is monitored during operation of the equipment 1 by means of a plausibility check or mutual comparison of the pressure measurements.

In order to do this, preferably when the right internal pressure has already been substantially reached and only pressure maintaining insufflation is being carried out, an operational state of the apparatus is produced, by closure of the proportional valve 8, in which substantially no gas flows out of the device. Then the drop in pressure at the particular flow resistor 5, 6 or 7, detected from the measurements of the pressure sensors 2 and 3, must be approximately equal to zero, i.e. operational pressure sensors 2, 3 must yield the same measurement. The creation of a differential value which is carried out in the microcontroller after the valve 8 has been shut must therefore yield the value zero (within a given error range).

If this is not the case a warning signal is emitted via the operating and display field 21 and/or by means of the control stage 10.2 there is automatic closure of a solenoid 13 (patient valve) provided at the exit from the equipment in the gas supply line 4 or another solenoid 14 (outlet valve) provided immediately downstream of solenoid 13 and connecting the gas supply line to atmosphere via a filter 15 is opened. (The filter 15 is intended to prevent foreign particles from outside from entering the insufflation system.)

Moreover, in order to check the function of the pressure sensors 2 and 3 it is also possible to carry out a slight increase or reduction in the gas flow periodically during insufflation by suitably actuating the proportional value 8 in accordance with a test cycle prescribed by the microcontroller 10.3. The resulting weak pressure wave must be indicated at the same level in properly operating pressure sensors 2, 3, i.e. there must be the same change in pressure. A simple comparison of amplitudes in the processor unit 10 will yield the test signal.

In order to protect the patient and the apparatus 1 for the purposes of gas insufflation a number of electrical overpressure switches 26a to 26c with different response values are provided between the flow resistors 5, 6, 7 and the first pressure sensor 2 on the gas supply line 4, these different response values being adapted to different conditions of use of the insufflation device and being selected as required by means of the operating field 21 before the instrument is used. Examples of response values are 50 mm Hg for switch 26a (for use in laparoscopy), 90 mm Hg for switch 26b (for arthroscopy) and 210 mm Hg for switch 26c (for hysteroscopy). The response thresholds may, if desired, be varied by means of the operating field and the processing and control unit.

If the initial pressure in the gas supply line 4 exceeds the value selected by the user, the microcontroller 10.3 is activated by an output signal from the corresponding overpressure switch 26a, 26b or 26c, and the control stage 10.2 emits, at its command, control signals which close the pressure regulator (the proportional valve) 8 and the solenoid valve 13 (patient valve) at the exit from the gas supply line 4 and open up the outlet valve 14 to allow the excess pressure to escape. Once this has happened the overpressure switch "drops" back, the outlet valve 14 is closed again, the proportional valve 8 and the patient valve 13 are reopened and insufflation is continued. The response threshold of the exhaust valve can also be variable—in another embodiment—by means of software using the control unit.

In addition, the patient valve 13 and outlet valve 14 can be used to carry out a self test of the apparatus 1. With the patient valve 13 closed and the outlet valve 14 closed, a specific quantity of gas is able to flow, via the pressure regulating device 8, to the pressure sensors 2 and 3 and to the pressure switches 26 in order to monitor function. If the outlet valve 14 is opened while the patient valve 13 remains closed, the function of the gas flow measurement can be checked. The corresponding control calculations are made by the microcomputer 10.3 which opens up the apparatus 1 after a positive functional check by means of a suitable output signal and signals that it is ready on the operating field 21.

The processing and control unit 10 is subdivided in structure into the relatively independent blocks 10.1, 10.2, 10.3 and 10.4 (already mentioned hereinbefore to some extent) which carry out analog signal processing (block 10.1—analog processing stage), pressure control or safety switching (block 10.2—control stage), the running of the operating program and all necessary calculations (block 10.3—microcontroller) and the supply of current to the apparatus (block 10.4—current supply unit).

As already mentioned hereinbefore, the microcomputer 10.3 has an associated operating and display field 21 by means of which the user can choose the mode of operation or working range of the apparatus and which indicates all the measurements and operating parameters calculated which are relevant to the user.

In addition, the microcomputer 10.3 may also be associated with an interface 22 by means of which the operator can be given access to the measurements or operating parameters in the form of a video feedback into the image screen in order to observe the medical intervention, and a gas conditioning device 23 for heating, humidifying and/or filtering as necessary, which is indicated by dotted lines in the Figure. Any external gas conditioning provided may also be controlled by the processing unit 10 of the insufflation device 1.

The versatility of the insufflation device 1 is further increased by the presence of a connection 19 for carrying out insufflation of the instruments, which means the introduction of gas into a surgical or diagnostic instrument for preventing body fluid from entering by the capillary effect and the insufflation pressure in the body cavity.

The quantity of gas required for this purpose is taken from the gas supply line 4 downstream of the pressure reducer 9, the quantity being regulated by a pressure regulator 17 in conjunction with a flow limiter 18. The connecting line 19 can be closed off by a separate valve 20. The pressure regulator 17 and the closure valve 20 are actuated by means of the microcontroller 10.3 and the control stage 10.2 The invention is not restricted in its realisation to the preferred embodiment described above. Rather, a number of alternative embodiments are conceivable which make use of the solution described whilst taking fundamentally different forms.

We claim:

1. Apparatus for introducing a fluid into a cavity or a blood vessel of a human or animal body, particularly for gas insufflation in preparation for or during a minimally invasive surgical procedure or investigation of the body cavity or blood vessel, said apparatus having a fluid supply line connected to a pressurized fluid store, this fluid supply line being associated with a pressure regulating device and, downstream thereof, a first pressure sensor which serves to determine the insufflation pressure, and a processing and control unit connected at the input end to the output of the pressure sensor and at the output end to a control input of the pressure regulating device, said apparatus further comprising a fluid flow measuring device which is associated with the fluid supply line and wherein the processing and control unit has a characteristic or table memory for storing at least one fluid flow correction characteristic or table and an internal pressure calculating unit connected at the input end to the output of the fluid flow measuring device and connected to the output of the characteristic or table memory, said processing and control unit further being adapted to determine the internal pressure produced in the body cavity or blood vessel from the insufflation pressure measured at a measuring point in the fluid introduction system and to determine a correction magnitude reflecting the drop in pressure between the measuring point and the body cavity or blood vessel, the correction magnitude being determined by taking into account a stored non-linear correlation, predetermined in the working area, between the fluid flow and the drop in pressure between the measuring point and the body cavity or blood vessel.

2. Apparatus according to claim 1, wherein, downstream of the pressure regulating device, on the fluid supply line, there is a second pressure sensor and between the measuring points of the first and second pressure sensors is provided a flow resistance element so that a fluid flow measuring device is formed by the first and second pressure sensors and the flow resistance element.

3. Apparatus according to claim 2, further comprising a plurality of flow resistance elements, particularly parallel-connected shutters or sintered inserts with different effective flow openings or flow resistance values, said flow resistance elements being arranged in branches of the fluid supply line and can be selectively switched into said branches by means of controllable valves provided for this purpose.

4. Apparatus according to claim 1, wherein the processing and control unit is designed to calculate the volume of fluid introduced per unit of time (fluid flow) from the difference in the pressure values obtained by the first and second pressure sensors.

5. Apparatus according to claim 1, further comprising controllable valves, said controllable valves being in the fluid supply line in the region of the end nearest the patient, so that the fluid supply line can be opened to the atmosphere or the outlet of the fluid supply line at the patient end can be closed off, in order to protect the patient.

6. Apparatus according to claim 1, wherein the processing and control unit is constructed so that correct operation of the pressure sensors is tested by comparison of the measurements supplied by the pressure sensors and that in the event of one of the pressure sensors being found to be defective a warning signal is emitted and/or a control signal is emitted, via a control unit to actuate a patient valve and/or an outlet valve associated with the fluid supply line.

7. Apparatus according to claim 1, further comprising at least two gas bottles as pressurized fluid stores which can be selectively connected to the fluid supply line via switching means.

8. Apparatus according to claim 7, further comprising a switching means for each gas bottle, said switching means being constructed as a solenoid with a non-return valve arranged downstream thereof.

9. Apparatus according to claim 1, wherein the processing and control unit has an analog processing part for the conditioning and analog processing of the measuring signals received from the pressure sensors and the control signals to be sent to adjusting members associated with the fluid supply line of the apparatus and a microcontroller cooperating therewith for controlling the operating program of the apparatus and for digitally processing the measurements.

10. Apparatus according to claim 1, further comprising a plurality of overpressure switches with differently preset response thresholds, said plurality of overpressure switches being provided on the fluid supply line and being selectively electrically actuatable, preferably by means of the processing and control unit.

11. Apparatus according to claim 1, wherein the fluid supply line has an additional outlet through which fluid can be introduced into a medical instrument.

12. Apparatus according to claim 11, further comprising in front of the additional outlet, a controllable valve for selectively closing the outlet and optionally for adjusting the fluid throughflow per unit of time.

13. Apparatus according to claim 1, further comprising a device for conditioning, particularly warming, humidifying and/or filtering the gas near the introduction instrument, said device preferably controlled by means of the processing and control unit.

14. Apparatus according to claim 1, wherein the processing and control unit has an associated interface for displaying data relating to the introduction of gas on a video screen for observation of an operating area.

* * * * *